(12) United States Patent
Foret et al.

(10) Patent No.: US 8,569,373 B2
(45) Date of Patent: Oct. 29, 2013

(54) COMPOSITIONS COMPRISING A C2-C14 CARBOXYLIC ACID AND A SURFACTANT FOR TREATING HOOF DISEASES

(75) Inventors: Chris Foret, Mission, KS (US); Alex Skender, Kansas City, MO (US); Fahim Ahmed, Greensboro, NC (US); Thomas C. Hemling, Kansas City, MO (US); N. Camelia Traistaru, Kansas City, MO (US)

(73) Assignee: DeLaval Holding AB, Tumba (SE)

( * ) Notice: Subject to any disclaimer, the term of this patent is extended or adjusted under 35 U.S.C. 154(b) by 762 days.

(21) Appl. No.: 12/440,409

(22) PCT Filed: Sep. 10, 2007

(86) PCT No.: PCT/US2007/077995
§ 371 (c)(1),
(2), (4) Date: May 28, 2010

(87) PCT Pub. No.: WO2008/031087
PCT Pub. Date: Mar. 13, 2008

(65) Prior Publication Data
US 2010/0234460 A1    Sep. 16, 2010

Related U.S. Application Data

(60) Provisional application No. 60/843,113, filed on Sep. 8, 2006, provisional application No. 60/888,243, filed on Feb. 5, 2007.

(51) Int. Cl.
*A61K 31/20* (2006.01)
*A61K 31/19* (2006.01)
*A61K 31/194* (2006.01)
*A61K 31/192* (2006.01)
*A61P 31/04* (2006.01)

(52) U.S. Cl.
USPC ............ 514/558; 514/557; 514/574; 514/568

(58) Field of Classification Search
None
See application file for complete search history.

(56) References Cited

U.S. PATENT DOCUMENTS

| 6,262,038 | B1 | 7/2001 | Pierce et al. | |
| 6,444,707 | B1 * | 9/2002 | Lampe et al. | 514/642 |
| 6,812,196 | B2 * | 11/2004 | Rees et al. | 510/238 |
| 2004/0048755 | A1 * | 3/2004 | Lopes | 510/111 |

FOREIGN PATENT DOCUMENTS

| WO | WO/0182694 | * 11/2001 |
| WO | 0207520 A | 1/2002 |
| WO | 03003832 A | 1/2003 |

OTHER PUBLICATIONS

European Examination Report for 07 842 133.6, dated Dec. 21, 2009, 5 pages.

* cited by examiner

*Primary Examiner* — Dennis Heyer
(74) *Attorney, Agent, or Firm* — Hovey Williams LLP

(57) ABSTRACT

Germicidal compositions containing at least one carboxylic acid combined with at least one nonionic or anionic surfactant, and methods of using the compositions for treatment or prevention of infectious hoof diseases are disclosed. The germicidal compositions remain active in the presence of manure, which eliminates the need to pre-clean the hooves before use. The compositions have particular utility for treating or preventing papillomatous digital dermatitis, interdigital phlegmon, interdigital dermatitis, laminitis, white line disease, heel erosion and other hoof diseases.

14 Claims, No Drawings

COMPOSITIONS COMPRISING A C2-C14 CARBOXYLIC ACID AND A SURFACTANT FOR TREATING HOOF DISEASES

RELATED APPLICATIONS

This application claims the benefit of priority to commonly-owned and U.S. Provisional Patent Application Nos. 60/843,113, filed 8 Sep. 2006, and 60/888,243, filed 5 Feb. 2007, each of which is incorporated herein by reference.

BACKGROUND

1. Field of the Invention

The present invention relates to compositions and methods for the control of hoof diseases. In particular, solutions effective in treating or preventing papillomatous digital dermatitis, interdigital phlegmon, interdigital dermatitis, laminitis, white line disease, heel erosion and other hoof diseases are disclosed.

2. Description of the Related Art

Infectious diseases of the hooves, such as hairy hoof warts (papillomatous digital dermatitis, or "PDD"), hoof rot (interdigital phlegmon), stable hoof rot (interdigital dermatitis), laminitis, white line disease and heel erosion are common in farm animals such as sheep, goats, horses, dairy cows and beef cattle. These diseases are a significant source of lameness, and produce a large economic and humane impact on the farming industry.

PDD is an infection of the epidermis of an animal's digit that is believed to be caused by *Treponema* organisms, which survive under the skin in conditions of low oxygen, temperatures between 30° C. and 37° C., and a pH range of 7.2 to 7.4. PDD infections range from painful, moist lesions to raised, hairy, wart-like lesions that can result in severe lameness, and even death, if not properly treated. With respect to dairy cows, hoof warts are also associated with losses in milk production, reproductive efficiency and body weight. Hoof rot, or interdigital phlegmon, is an infection of the soft tissue between the claws of the feet, where bacteria invade the skin of the foot at injured or damaged skin areas. Initially, the infection causes a painful swelling of the skin between the claws. A fissure or crack then develops along the swollen area for part or all of the length of the interdigital space. If left untreated, hoof rot can enter the joints, bones, and/or tendons of the foot, making recovery from the infection unlikely. Animals with hoof rot can have a mild fever, loss of appetite and accompanying weight loss, and develop mild to severe lameness. Interdigital dermatitis, or stable hoof rot, is generally a chronic inflammation of the skin in the interdigital cleft. The condition may cause lameness or heel crack/heel erosion. These three hoof diseases—papillomatous digital dermatitis, interdigital phlegmon and interdigital dermatitis—are caused by bacterial infections, and they may be accompanied by or lead to complications with other hoof diseases such as laminitis, white line disease and heel erosion.

Treatment or prevention of hoof diseases generally involves topical application of antibiotics to affected areas. However, antibiotics are expensive, and, particularly when treating cattle, concerns related to the presence of antibiotics in beef and milk arise. Further, it is well known that extended use of antibiotics leads to antibiotic-resistance, and the development of more aggressive strains of bacteria.

The use of chemical germicides to treat or prevent hoof diseases is also common. For example, germicidal compositions containing copper sulfate, zinc sulfate, sulfamethazine, quaternary ammonium compounds, hydrogen peroxide and/or peracetic acid are known.

Application of the antibiotic or germicidal compositions is typically carried out by making the animals walk through a footbath. However, after a few animals have passed through the footbath, the solution becomes contaminated with manure. Many formulas that are currently used for footbath solutions loose their activity in the presence of manure. As a result, these baths can become a breeding ground for bacteria, and can accelerate the spread of infectious hoof diseases, rather than prevent them. Infectious hoof diseases can also be treated by a topical spray, footwrap or application of a foam or gel. However, the hoof is likely to be highly contaminated with manure, dirt or other soils before and/or shortly after application.

Other germicides, such as iodine or chlorine, are extremely effective disinfectants for other purposes, but they are not useful for a footbath solution because they quickly react with manure, which reduces the efficacy of the active ingredients. Germicides such as salicylic acid are also ineffective for footbath solutions due to limited solubility.

SUMMARY

The present invention advances the art and overcomes the problems outlined above by providing highly efficacious disinfectant solutions for the treatment and/or prevention of hoof diseases. The disclosed solutions are substantially unaffected by the presence of manure, and may be used on hooves in their natural (uncleaned) state. Methods for using the solutions to treat or prevent hoof diseases are disclosed.

In one embodiment, an aqueous composition for treatment or prevention of infectious hoof diseases includes a therapeutically effective amount of a $C_2$-$C_{14}$ carboxylic acid and an effective amount of a surfactant, the surfactant selected from nonionic and anionic surfactants. The composition retains germicidal activity in the presence of greater than 10% manure.

In one embodiment, an aqueous composition for treatment or prevention of infectious hoof diseases consists essentially of a therapeutically effective amount of a $C_2$-$C_{14}$ carboxylic acid and an effective amount of a surfactant, the surfactant selected from nonionic and anionic surfactants. The composition retains germicidal activity in the presence of greater than 10% manure.

In one embodiment, a method for treating or preventing infectious hoof diseases includes topically administering a therapeutically effective amount of an aqueous composition comprising a $C_2$-$C_{14}$ carboxylic acid and an effective amount of a surfactant, the surfactant selected from nonionic and anionic surfactants, to one or more hooves of an animal. The step of administering occurs with the hoof or hooves in a natural state.

DETAILED DESCRIPTION

There will now be shown and described compositions and methods for treating or preventing hoof diseases. In particular, it has been found that under acidic conditions, compositions containing one or more carboxylic acids in combination with one or more anionic and/or nonionic surfactants retain germicidal activity in the presence of a significant quantity of manure.

Concentrations disclosed throughout this application are based on ready-to-use compositions, except where otherwise stated. Those of skill in the art will appreciate that such compositions may be manufactured and/or sold in concentrated forms that are suitable for dilution prior to use. Manipulation of the concentration of the disclosed compositions is within the level of ordinary skill in the art.

In one embodiment, an aqueous composition for the treatment or prevention of infectious hoof diseases contains a $C_2$-$C_{14}$ carboxylic acid, such as a $C_2$-$C_{14}$ fatty acid or a hydroxyl carboxylic acid, in combination with a surfactant selected from nonionic and anionic surfactants. As used herein, a "fatty acid" is a carboxylic acid with a carbon chain, that may be saturated or unsaturated, which generally contains at least three carbon atoms. A "hydroxyl carboxylic acid", as used herein, is a carboxylic acid that contains one or more hydroxyl groups that are not part of the acid moiety. The carboxylic acid may be present in an amount from about 0.01% to about 90% by weight of the composition, or from about 0.01% to about 50% by weight, or from about 0.01% to about 30% by weight, or from about 0.01% to about 4% by weight, or from about 0.2% to about 1%. The surfactant may be present from about 0.01% to 40% by weight, or from about 0.01% to 20% by weight, or from about 0.01% to 10% by weight, or from about 0.01% to about 4%, or from about 0.2% to about 1%. The resulting germicidal composition may be used to treat animal hooves that are presented in their natural state. Hooves in their natural state may be soiled with particulate matter, such as dirt and manure, and/or microscopic pathogens, such as bacteria. For example, the present compositions remain effective in the presence of greater than 10% manure, or greater than 20% manure. Use of the present compositions on hooves in their natural state eliminates the need for a pre-treatment or pre-cleaning step, and therefore provides a significant cost and time advantage over known compositions.

In one embodiment, a composition for treatment or prevention of hoof diseases comprises a therapeutically effective amount of at least one carboxylic acid and at least one surfactant, and optionally additional germicides selected from the group consisting of N,N-bis(3-aminopropyl) $C_6$-$C_{18}$ alkyl amines, bronopol, chlorhexidine salts, triclosan, glycolic acid, lactic acid, polyhexamethyl biguanide, polyhexamethylene guanidine hydrochloride, polyhexamethylene guanidine hydrophosphate, poly[2-(2-ethoxy)-ethoxyethyl]-guanidinium chloride, benzyl alcohol, benzoic acid and mixtures thereof.

In another embodiment, an aqueous composition for treatment or prevention of infectious hoof diseases consists essentially of a therapeutically effective amount of at least one carboxylic acid and at least one surfactant. Optionally, additional ingredients that do not materially alter the germicidal properties of the composition may be added. Such additional ingredients may include one or more of a pH adjusting agent, a wetting agent, a foaming agent, a dye, a viscosity control agent, a preservative, a skin conditioning agent, a coupling agent and a solvent.

Preferred compositions provide a substantial reduction, e.g., greater than 99% or preferably 99.99%, in Gram positive and Gram negative bacterial populations. Exemplary bacteria that contribute to hoof infections include *Bacteroides spp, Bacteriodes melaningenicus, Campylobacter faecalis, Clostridium* spp, *Fusobacterium* spp, *Peptococcus asaccharolyticus, Peptostreptococcus* spp, *Serpens* spp, *Treponema* spp, *Bacteroides thetaictaomicron, Fusobacterium necrophorum, Prevotella melaningenicus, Porphyromonas asaccharolytica, Porphyromonas levii, Porphyromonas melaminogenicus, Dichelobacter fragilis, Arcanobacterium pyogenes, Dichelobacter nodosus* and *Porphyromonas necrophorum*. The quantity of a composition that achieves a substantial reduction in a bacterial population is considered an effective amount of the composition for treating or preventing infectious hoof diseases.

As discussed above, solutions for the treatment or prevention of infectious hoof diseases can be supplied either as ready-to-use products or as concentrates for dilution at the point of use. The present compositions are generally acidic and have a pH less than about 5, preferably between 2 and 3.5. Generally, the pH may be adjusted to any value that is desired in the intended environment of use by the addition of acid, base or buffer.

A broader object of the disclosed instrumentalities is to provide a germicidal composition that may be used, for example, according to any purpose for antibacterial or bactericidal properties. In a particular embodiment, the composition is intended to be used as a footbath for treating animal hooves. In other embodiments the composition is intended to be used as a hand sanitizer, a skin cleanser, a surgical scrub, a wound care agent, a disinfectant, a bath/shower gel, a hard surface sanitizer and the like. Preferred compositions for skin applications have a pH of about 2.5 to about 7 and provide a substantial reduction, e.g., greater than 99%, in Gram positive and Gram negative bacterial populations. It will be understood, however, that different uses may prompt different pH targets. For example, compositions adapted for hard surfaces may exhibit low pH values, such as 1.0 or 0.5.

The phrase "therapeutically effective amount" is intended to qualify the amount of the topical composition which will achieve the goal of decreased microbial concentration. "Therapeutically effective" may also refer to improvement in disorder severity or the frequency of incidence over no treatment.

The term "topical" shall refer to any composition which may be applied to the epidermis, keratin or other animal portion.

The term "additive" shall mean any component that is not a germicide or a solvent used to dilute or solubilize the components of the composition.

The germicidal activity of a large number of ingredients has been tested for the ability to kill *Escherichia coli* and *Staphylococcus aureus* in mixtures that have been contaminated with 10% and 20% manure. *E. coli* and *S. aureus* were chosen as representative bacteria for screening purposes. Solutions of the mixtures with 10% manure and bacteria were prepared, and the reduction in the concentration of bacteria was determined after 30 seconds and again after 5 minutes. In addition, the formulas were evaluated for skin irritation based on in vitro test data. The testing method used was that of Wolfgang J. W. Pape, Udo Hoppe: In vitro Methods for the Assessment of Primary Local Effects of Topically Applied Preparations. *Skin Pharmacol.* (1991), 4: 205-212, which is incorporated herein by reference. Based on this data, various components were selected for use in aqueous disinfectant solutions, such as footbaths.

Those of skill in the art will appreciate that variability in manure composition occurs due to differing diets, physiology, habitat, the presence or absence of diseases or pathogens and the like between animals. Trials conducted herein were performed in the presence of an exemplary manure sample, and showed excellent germicidal activity. If in practice, however, it becomes necessary to adjust the disclosed compositions to accommodate for variations in manure, such adjustment is within the level of skill of the ordinary artisan.

Carboxylic Acids

Carboxylic acids that are suitable for use as germicides in the present compositions include, but are not limited to, $C_2$-$C_{14}$ fatty acids, such as propanoic acid (propionic acid), butanoic acid (butyric acid), pentanoic acid, hexanoic acid (caproic acid), heptanoic acid, octanoic acid (caprylic acid), nonanoic acid, decanoic acid (capric acid), endecanoic acid, dodecanoic acid (lauric acid), tridecanoic acid and tetradecanoic acid (myristic acid), and organic acids, such as lactic acid, citric acid, benzoic acid, malic acid, oxalic acid, tartaric acid, succinic acid, glutaric acid, valeric acid, glycolic acid and the like. One or more of these carboxylic acids may be used in the present compositions to achieve a therapeutic effect.

Surfactants

Surfactants that have shown unexpected synergy with carboxylic acids in the present compositions include, but are not limited to, alkyl sulfates, such as sodium lauryl sulfate; alkyl aryl sulfates; alkyl aryl sulfonates; alkyl sulfonates, such as sodium octane sulfonate; and alcohol ethoxylates, such as $C_9$-$C_{11}$ pareth-8. The nonionic surfactant $C_9$-$C_{11}$ pareth-8 is a primary alcohol ethoxylate having an average of about 8 moles of ethylene oxide per mole of alcohol. One or more of these surfactants may be used in the present compositions to achieve a therapeutic effect.

Carboxylic Acid/Surfactant Combinations

Preferred carboxylic acid/surfactant combinations include, without limitation: lactic acid with sodium lauryl sulfate; lactic acid with sodium octane sulfonate; lactic acid with sodium lauryl sulfate and sodium octane sulfonate; citric acid with sodium lauryl sulfate; citric acid with sodium octane sulfonate; citric acid with sodium lauryl sulfate and sodium lauryl sulfonate; $C_2$-$C_{14}$ fatty acids with $C_9$-$C_{11}$ pareth-8; $C_2$-$C_{14}$ fatty acids with sodium lauryl sulfate; $C_2$-$C_{14}$ fatty acids with sodium octane sulfonate; and $C_2$-$C_{14}$ fatty acids with sodium lauryl sulfate and sodium lauryl sulfonate.

It will be appreciated by those skilled in the art that the sodium salts specifically mentioned above may be replaced with other salts of the disclosed compounds. For example, potassium lauryl sulfate, potassium octane sulfonate, ammonium lauryl sulfate and ammonium octane sulfonate may be substituted for the sodium salts mentioned above.

Germicides

A preferred composition includes from 0% to 25% by weight of at least one germicide. Throughout this disclosure, the term "germicide" shall be used to describe a composition which, when used alone or in combination with other germicides, accelerates the demise or limits the growth or replication of microorganisms, particularly bacteria. Examples of suitable germicides include N,N-bis(3-aminopropyl) $C_6$-$C_{18}$ alkyl amines (such as N,N-bis(3-aminopropyl)dodecylamine), bronopol (2-bromo-2-nitro-1,3-propanediol), chlorhexidine salts, triclosan (2,4,4'-trichloro-2'-hydroxydiphenylether, may be purchased from Ciba Specialty Chemicals as IRGASAN™ and IRGASAN DP 300™), glycolic acid, lactic acid, benzyl alcohol, benzoic acid, polyhexamethyl biguanide (CAS 32289-58-0), guanidine salts such as polyhexamethylene guanidine hydrochloride (CAS 57028-96-3), polyhexamethylene guanidine hydrophosphate (89697-78-9), and poly[2-(2-ethoxy)-ethoxyethyl]-guanidinium chloride (CAS 374572-91-5) and mixtures thereof.

In one embodiment, the disclosed germicides may be used in combination with traditional germicides such as copper sulfate, zinc sulfate, sulfamethazine, quaternary ammonium compounds, hydrogen peroxide and/or peracetic acid, for example, to achieve an effective kill at lower concentrations of traditional germicides.

Acids

In addition to the carboxylic acids discussed above, mineral acids having efficacy against microorganisms, particularly bacteria, and minimal irritation of the skin may be incorporated into the present compositions. Examples of suitable mineral acids include sulfuric acid, sulfurous acid, sulfamic acid, hydrochloric acid, phosphoric acid and phosphorous acid.

The aforementioned compositions may be supplemented by buffering agents, pH adjusting agents, emollients, preservatives, surfactants or wetting agents, dyes, foaming agents, viscosity modifying agents, stabilizers, perfumes, co-solvents, coupling agents and mixtures thereof. These may be present in any suitable amount.

pH Adjusting Agents

It will be appreciated that at least one carboxylic acid is present as an active germicide in the present compositions, and that that acid will affect the pH of the composition. The pH of the composition may, however, be adjusted by the addition of acidic, basic or buffering agents. Suitable acids for use as pH adjusting agents may include, for example, sulfuric acid, sulfurous acid, sulfamic acid, hydrochloric acid, phosphoric acid, phosphorous acid, $C_1$-$C_4$ fatty acids, citric acid, glycolic acid, lactic acid, acetic acid, benzoic acid, malic acid, oxalic acid, tartaric acid, succinic acid, glutaric acid, valeric acid, glycolic acid and the like. The pH may be raised, or made more alkaline, by addition of an alkaline agent such as sodium hydroxide, ammonium hydroxide, potassium hydroxide, sodium carbonate, sodium bicarbonate, monosodium acid diphosphonate or combinations thereof. Traditional acid buffering agents such as citric acid, lactic acid and phosphoric acid may also be used to maintain a desired pH.

Wetting Agents

Wetting agents may be included in the disclosed formulations. Typical wetting agents are used to wet the surface of application, thereby reducing surface tension so that the product can easily contact the surface. The wetting agents of the formulation increase overall detergency of the formula, solubilize or emulsify organic ingredients that otherwise would not dissolve or emulsify, and facilitate penetration of active ingredients deep into depressions of the surface, which may be an animal hoof.

Suitably effective wetting agents may include anionic, nonionic, zwitterionic and amphoteric surfactants. Wetting agents and surfactants suitable for use in the disclosed formulations can be high foaming, low foaming and non-foaming. Suitable anionic surfactants can be chosen from alkyl sulfonic acid, an alkyl sulfonate salt, a linear alkyl benzene sulfonic acid, a linear alkyl benzene sulfonate, an alkyl α-sulfomethyl ester, an α-olefin sulfonate, an alcohol ether sulfate, an alkyl sulfate, an alkylsulfo succinate, a dialkylsulfo succinate, or alkali metal, alkaline earth metal, amine and ammonium salts thereof. Specific examples are linear $C_{10}$-$C_{16}$ alkylbenzene sulfonic acid, linear $C_{10}$-$C_{16}$ alkylbenzene sulfonate or alkali metal, alkaline earth metal, amine and ammonium salts thereof, e.g., sodium dodecylbenzene sulfonate, sodium $C_{14}$-$C_{16}$ α-olefin sulfonate, sodium methyl α-sulfomethyl ester and disodium methyl α-sulfo fatty acid salts. Suitable nonionic surfactants can be chosen from alkyl polyglucoside, alkyl ethoxylated alcohol, alkyl propoxylated alcohol, ethoxylated-propoxylated alcohol, sorbitan, sorbitan ester and alkanol amide. Specific examples include $C_8$-$C_{16}$ alkyl polyglucoside with a degree of polymerization ranging from 1 to 3 e.g., $C_8$-$C_{10}$ alkyl polyglucoside with a degree of polymerization of 1.5 (Glucopon® 200), $C_8$-$C_{16}$ alkyl polyglucoside with a degree of polymerization of 1.45 (Glucopon® 425), $C_{12}$-$C_{16}$ alkyl polyglucoside with a degree of polymerization of 1.6 (Glucopon® 625), and polyethoxylated polyoxypropylene block copolymers (poloxamers) including by way of example the Pluronic® poloxamers commercialized by BASF Chemical Co. Amphoteric surfactants can be chosen from alkyl betaines and alkyl amphoacetates. Suitable betaines include cocoamidopropyl betaine, and suitable amphoacetates include sodium cocoamphoacetate, sodium lauroamphoacetate and sodium cocoamphodiacetate.

Foaming Agents

A foaming agent may be used in the disclosed antimicrobial compositions. A foaming agent aerates a liquid composition to produce a foam that may increase surface area of the composition and improve adherence with the surface to be treated (e.g., an animal hoof). Typically, a high foaming surfactant such as sodium lauryl sulfate, dodecylbenzene sulfonic acid, sodium alkylaryl polyether sulfate, sodium lauryl ether sulfate, sodium decyl sulfate, cocamine oxide, $C_{12}$-$C_{14}$ whole coconut amido betaines can be used to generate a stable foam. The foam is produced when agitation in the form of a compressed gas is mixed with the solution either by bubbling the gas into the solution or spraying the solution or solution-gas mixture through spray equipment. Suitable gases include but are not limited to nitrogen, air, carbon dioxide and mixtures thereof. Foam can also be generated by the mechanical action of animals walking through the composition, or by other mechanical means that mix atmospheric air with the composition. The composition can be applied by having animals walk through an area containing the foam or by having the animal walk through a footbath solution that has foam floating on top of the solution.

Dyes

One or more dyes may be included in the composition. Color on an animal's hoof or hooves may serve as an indicator that a particular animal has been treated. To preclude any problems with possible contamination of milk, for example, in the event that the dye contacts the animal's teats or enters the animal's circulatory system, only FD&C Certified (food grade) dyes should be used. There are many FD&C dyes available, such as FD&C Red #40, FD&C Yellow #6, FD&C Yellow #5, FD&C Green #3, FD&C Blue #1, FD&C Orange #4 and combinations thereof.

Viscosity Modifying Agents

Solution viscosity may be thinned by the addition of water or co-solvent; however, the compositions, especially gel forms, may benefit from the use of a viscosity modifying agent in an amount generally ranging from 0.1% to about 10% by weight of the composition. Viscosity of the composition preferably ranges from 1 cPs to 10000 cPs at ambient temperature. The viscosity referred to throughout this application is Brookfield viscosity measured in cPs by a Brookfield LV viscometer at ambient temperature (25° C.) with a spindle #2 @ 3 to 30 rpm. In various embodiments, a thickener may be added to achieve a viscosity range of from 50 cPs to 10000 cPs, or from 1000 cPs to 4000 cPs.

Viscosity modifying agents include plant gum materials such as guar gum; starch and starch derivatives, for example, hydroxyethyl starch or cross-linked starch; microbial polysaccharides, for example, xanthan gum or seaweed polysaccharides, such as sodium alginate, carrageenan, curdlan, pullulan or dextran; whey; gelatin; chitosan; chitosan derivatives; polysulfonic acids and their salts; polyacrylamide; and glycerol. Cellulosic thickeners may be used including hemicellulose, for example arabinoxylanes and glucomannanes; cellulose and derivatives thereof, for example methyl cellulose, ethyl cellulose, hydroxyethyl cellulose or carboxymethyl cellulose.

Preservatives

Preservatives may be added to the compositions. For example, ethylenediaminetetraacetic acid (EDTA) and its alkali salts act as chelating agents to bind metal ions that would otherwise facilitate metalloenzyme reactions that produce energy for bacterial cell replication. Other traditional preservatives may be used, for example, paraban, methyl paraban, ethyl paraban, glutaraldehyde, etc. Preservatives such as an alcohol can also be added. The alcohol, in embodiments, may be benzyl alcohol, a low molecular weight alcohol having a carbon number less than five, and combinations thereof.

Skin Conditioning Agents

Skin conditioning agents may also be optionally used in the disclosed compositions. Skin conditioning agents may provide extra protection for human or animal skin prior to or subsequent to being exposed to adverse conditions. For example, skin conditioning agents may include moisturizers, such as glycerin, sorbitol, propylene glycol, Laneth-5 to 100, lanolin alcohol, D-panthenol, polyethylene glycol (PEG) 200-10,000, polyethylene glycol esters, acyl lactylates, polyquarternium-7, glycerol cocoate/laurate, PEG-7 glycerol cocoate, stearic acid, hydrolyzed silk peptide, silk protein, guar hydroxypropyltrimonium chloride, alkyl poly glucoside/glyceryl laurate, shea butter and coco butter; sunscreen agents, such as titanium dioxide, zinc oxide, octyl methoxycinnamate (OMC), 4-methylbenzylidene camphor (4-MBC), avobenzone, oxybenzone and homosalate; and itch-relief or numbing agents, such as aloe vera, calamine, mint, menthol, camphor, antihistamines, corticosteroids, benzocaine and paroxamine HCl.

Coupling Agents

In some embodiments, a composition may contain a coupling agent that facilitates dissolution of one or more components, e.g., surfactants or fatty acids that would otherwise be insoluble or only sparingly soluble in the solvent. Coupling agents generally contain short chained ($C_2$-$C_6$) moieties linked to bulky hydrophilic groups, such as hydroxyl and/or sulfonate groups. Exemplary coupling agents include aryl sulfonates such as sodium naphthalene sulfonate, sodium octane sulfonate, sodium xylene sulfonate, and ammonium octane sulfonate, as well as some phosphate esters.

Solvents

The preferred solvent for the present composition is water. However, one skilled in the art will recognize that solvents or co-solvents other than water may be used to serve the same purpose. In some embodiments, a composition may contain at least about 5% by weight water and preferably at least about 10% by weight water based on the total weight of the composition. Propylene glycol, ethylene glycol, glycerine and alcohols can also be used as solvents either alone or in combination with water.

In one embodiment, a method for treating or preventing infectious hoof diseases includes topically administering a therapeutically effective amount of an aqueous germicidal composition comprising a carboxylic acid and a surfactant selected from anionic and nonionic surfactants. The composition may be administered as a liquid, a spray, a foam, a gel, an ointment, a cream, a footbath, a footwrap coated with the composition, or any other topical form acceptable to the industry.

EXAMPLES

Methods

The activity of germicidal compositions was tested by a procedure involving preparing a test tube containing 1 g (10%) or 2 g (20%) of manure, 9.9 mL of germicide and 0.1 mL of ~$1\times10^7$ bacteria. The reagents within the test tube were mixed for 30 seconds and then 0.1 mL of the mixture was added to a 6 mL well of a microwell plate containing 0.9 mL neutralizer. After mixing with the neutralizer, 4.5 mL of agar was added to the well. The microwell plate was then incubated for 24 hr to 48 hr. A visual score for the concentration of bacteria was recorded. A score of 5 indicated complete kill of bacteria when no colonies of growth were observed in the well. A score of 0 indicated no kill when numerous colonies of bacteria were observed. The score was determined by a visual comparison to standards which did not contain a germicide (score=0) or which had no bacteria added (score=5). Duplicate samples were randomly distributed in the microwell plate so that each visual observation was made twice without knowledge of the identity of the sample contained in each well. This method for the visual determination of sanitizer efficacy has given reproducible results. The reproducibility can be noted in the results for the duplicate trials in Table 1 A-H and duplicate results on separate preparations in Table 3-V and Table 4-X.

Bacteria Testing

Additional experiments were performed to test the germicidal properties of the disclosed compositions using a modified version of the AOAC sanitizer test (Association of Official Analytical Chemists. 1990. Official Methods of Analysis, Pages 138-140 in Germicidal and Detergent Sanitizing Action of Disinfectants 960.09, Vol. I. 15$^{th}$ ed. AOAC, Arlington, Va.). According to this procedure, manure was collected from a dairy farm, dispensed into flasks and autoclaved at 121° C. and 17 psi for 30 minutes. Manure samples were then stored in a freezer until needed. When needed, manure was thawed at room temperature then dispensed into 250 mL Erlenmeyer flasks in amounts appropriate for the challenge desired (10 g for 10% manure, 20 g for 20% manure, etc.). The flasks with manure, and any empty flasks needed, were capped with aluminum foil and autoclaved at 134° C. and ~20 psi for 4 min.

Freeze-dried pellets of *E. coli* (ATCC 11229) and *S. aureus* (ATCC 6538) were hydrated, placed in test tubes containing nutrient agar and incubated at 37° C. for 24 hours. Sterile buffer (0.25 M phosphate adjusted to pH 7.2) was used to dilute and transfer the bacteria to additional nutrient agar tubes, which were incubated for another 24 hours. *S. aureus* was then diluted with buffer and transferred to nutrient agar in French bottles, and *E. coli* was diluted and transferred to fresh nutrient agar tubes. Both types of bacteria were incubated at 37° C. for 72 hours. *E. coli* was then diluted and transferred to nutrient agar in French bottles. Sterile buffer and glass beads were added to the *S. aureus* French bottles and the solution was vacuum filtered through a #2 filter. The resulting bacterial suspension had a concentration of approximately $10^8$ cfu/mL. After 24 hours, the *E. coli* suspension was collected in the same manner.

Germicide sample solutions were prepared and dispensed into the flasks containing manure. For tests without manure, 99 mL of germicide were added to an empty, sterile, 250 mL flask. For a 10% manure challenge, 89 mL of germicide were added to a flask prepared with 10 g of manure, and 79 mL of germicide were added to flasks with 20 g of manure for a 20% manure challenge.

When all flasks with manure and germicide solution were prepared, 1 mL of approximately $10^8$ cfu/mL bacteria suspension was mixed into the first test flask and a timer was started to monitor the contact time. After the desired contact time, 1 mL of the solution of bacteria, germicide and manure was added to a test tube containing 9 mL of a neutralizer appropriate for the germicide. Three serial dilutions were made of this solution and 1 mL of each solution was dispensed into a Petri dish in duplicate. Also, 0.1 mL of the most dilute solution was dispensed in duplicate. Approximately 15 mL of sterile tryptone glucose extract agar was added to each Petri dish and when solidified, each plate was incubated at 37° C. for 48 hours. This procedure was repeated for all samples to be tested.

For controls, the $10^8$ cfu/mL bacteria suspensions were diluted to concentrations of $10^4$ and $10^3$ cfu/mL. One milliliter of the $10^4$ cfu/mL dilution and 0.1 mL of the $10^3$ cfu/mL dilution (done in triplicate) were dispensed onto Petri dishes and approximately 15 mL of tryptone glucose extract agar was added. When solidified, the plates were incubated at 37° C. for 48 hours. An average of the plate counts for the triplicate platings of the $10^3$ cfu/mL dilution was considered the initial numbers control count.

The results were obtained after 48 hours, all plates were counted following standard counting procedures. Percent reduction was calculated using the following formula:

$$\frac{(IC - SC) * 100}{IC}$$

where:

$IC$ = Initial Numbers Control Count (cfu/mL)

$SC$ = Test Substance Control Count (cfu/mL)

The percent reduction was then converted into a log kill value.

Irritation Testing

Irritation tests were performed to determine whether or not the disclosed compositions would be mild enough for topical application. These tests involved two measurements made on fresh calf blood, where red blood cells were isolated by adding 50 mL of sodium citrate buffer (17.03 g trisodium citrate+ 8.45 g citric acid diluted to 1 L with bacteria-free DI water) to every 450 mL of blood, then repetitively washing with sodium citrate buffer and centrifuging to remove white blood cells and plasma.

Compositions disclosed herein were introduced into a container containing the isolated red blood cells and values for Haemolysis ($H_{50}$); a Denaturation Index value (DI); and a Lysis/Denaturation Ratio (L/D) were determined using methods disclosed by Wolfgang J. W. Pape, Udo Hoppe: In vitro Methods for the Assessment of Primary Local Effects of Topically Applied Preparations. *Skin Pharmacol.* (1991), 4: 205-212. The haemolysis—or tendency of the red blood cells to rupture when in contact with the test product—was measured by the half-haemolysis value $H_{50}$. The denaturation of protein caused by the test product was measured by the denaturation index (DI). The overall irritation value for a product was determined by the ratio of the $H_{50}$/DI which is referred to as the lysis/denaturation quotient. The overall irritation score is given by the lysis/denaturation value which is calculated by the equation: L/D=$H_{50}$ (measured in ppm)/DI (measured in %).

The $H_{50}$ value which measures haemolysis alone usually shows a similar irritation correlation to the L/D ratio. The higher the ppm value for $H_{50}$ the less irritating the product. A crude scale is $H_{50}$>500 ppm (non-irritant); 120-500 (slight irritant), 30-120 (moderate irritant), 10-30 (irritant) and 0-10 (strong irritant).

The DI score which measures denaturation of protein also shows a correlation to the L/D ratio. A crude scale is DI 0-5% (non-irritant); 5-10% (slight irritant), 10-75% (moderate irritant), 75-100% (irritant) and >100% (strong irritant).

The L/D ratio is the primary value used to determine irritation. An L/D value greater than 100 is an indication that the formulation is a non-irritant; levels between 10 and 100 are considered slight irritants; levels between 1 and 10 are considered moderate irritants; levels between 0.1 to 1 are considered irritants; and levels lower than 0.1 are considered strong irritants. A practical upper limit for the L/D ratio is about 1,000,000.

Example 1

Tables 1 and 2 show germicidal compositions A-Q containing fatty acid germicides. Specifically, combinations of Emery 658 ($C_8$-$C_{10}$ fatty acid) with $C_9$-$C_{11}$ pareth-8 were tested for germicidal activity. The nonionic surfactant $C_9$-$C_{11}$ pareth-8 is a primary alcohol ethoxylate having an average of about 8 moles of ethylene oxide per mole of alcohol.

In trials A-Q, formic acid was used to acidify the compositions and dissolve the fatty acid. Based on measured L/D ratios, the majority of these compositions were slightly irritating. However, Composition H, which contained relatively high concentrations of a hydroxyl carboxylic acid (citric acid), produced a higher (less irritating) L/D ratio than compositions that did not contain a hydroxyl carboxylic acid or that contained lower concentrations of a hydroxyl carboxylic acid (se, e.g., Compositions F and G, Table 1).

Use of propionic acid, in conjunction with formic acid, to acidify the compositions and dissolve the fatty acids, also produced high (non-irritating) L/D values (see, e.g., Compositions O-Q, Table 2).

Tables 3-5 show compositions containing lactic acid, one or more anionic surfactants and, optionally, a fatty acid. For comparison, lactic acid alone provides minimal germicidal activity in the presence of manure (Composition U, Table 3). Likewise, Compositions S and EE of Tables 3 and 5, respectively, demonstrate that the anionic surfactants sodium lauryl sulfate and sodium octane sulfonate used alone provide little or no germicidal activity. However, lactic acid combined with each of these anionic surfactants (compositions R and V of Table 3) provides a synergistic composition with good germicidal activity. Further, lactic acid combined with sodium lauryl sulfate (Composition CC, Table 5) remains effective in the presence of manure, even when used at low concentrations (0.5%).

Tables 1-5 further illustrate that additional germicides can be added to compositions containing lactic acid and an anionic surfactant to achieve a higher kill value. For example, Composition BB (Table 4), which contains glutaraldehyde, increases the log reduction in *E. coli* versus Composition V (Table 3), which contains only lactic acid and sodium octane sulfonate. In another example, Composition W (Table 4) shows a combination of lactic acid and bronopol that provides good germicidal activity, even though lactic acid alone (Composition U, Table 3) and a similar bronopol composition without lactic acid (Composition Y, Table 4) both show poor germicidal activity.

TABLE 1

COMPOSITIONS CONTAINING FATTY ACIDS (% W/W)

|  | A | B | C | D | E | F | G | H |
|---|---|---|---|---|---|---|---|---|
| Water | 0 | 2 | 2 | 2 | 0 | 7 | 5 | 12 |
| Formic acid, 90% | 80 | 80 | 70 | 60 | 70 | 70 | 70 | 60 |
| $C_9$-$C_{11}$ pareth-8 | 10 | 10 | 10 | 10 | 10 | 10 | 10 | 10 |
| Emery 658 | 10 | 8 | 8 | 8 | 10 | 8 | 10 | 8 |
| Sulfuric acid, 96% |  |  | 10 | 20 | 10 |  |  |  |
| Citric acid, 100% |  |  |  |  |  | 5 | 5 | 10 |
| TOTAL | 100 | 100 | 100 | 100 | 100 | 100 | 100 | 100 |
| Physical stability after 1 month at 25° C. | OK | OK | clear light brown | clear light brown | yellow or brown | OK | OK | OK |
| Physical stability after 1 month at 50° C. | pale yellow | pale yellow | clear brown | clear brown | brown | light brown | light brown | light brown |
| Log kill *S. aureus* diluted 1 + 49 with 10% manure max kill value 5 | 5/5 Trial 1/ Trial2 | 5/5 | 5/5 | 5/5 | 5/5 | 5/5 | 5/5 | 5/5 |
| Log kill *E. coli* diluted 1 + 49 with 10% manure max kill value 5 | 5/5 | 4.5/4.5 | 5/5 | 5/5 | 5/5 | 5/5 | 4/5 | 5/5 |
| pH | 3.09 | 3.21 | 2.45 | 2.42 | 2.84 | 3.31 | 3.25 | 3.15 |
| L/D Ratio | 387 | 459 | 395 | 620 | 588 | 472 | 461 | 927 |

TABLE 2

COMPOSITIONS CONTAINING FATTY ACIDS (% W/W)

|  | I | J | K | L | M | N | O | P | Q |
|---|---|---|---|---|---|---|---|---|---|
| Formic acid, 90% | 70 | 70 | 60 | 60 | 60 | 50 | 60 | 60 | 40 |
| $C_9$-$C_{11}$ pareth-8 | 10 | 10 | 10 | 10 | 10 | 10 | 10 | 10 | 10 |
| Emery 658 | 8 | 10 | 8 | 8 | 10 | 8 | 8 | 10 | 8 |
| Lactic acid, 88% | 10 | 10 | 20 |  |  |  |  |  |  |

TABLE 2-continued

COMPOSITIONS CONTAINING FATTY ACIDS (% W/W)

|  | I | J | K | L | M | N | O | P | Q |
|---|---|---|---|---|---|---|---|---|---|
| Hydrochloric acid, 37% |  |  |  | 20 | 20 | 30 |  |  |  |
| Propionic acid, 100% |  |  |  |  |  |  | 20 | 20 | 40 |
| TOTAL (adjusted with water) | 100 | 100 | 100 | 100 | 100 | 100 | 100 | 100 | 100 |
| Physical stability after 1 month at 50° C. | light brown | light brown | light brown | cloudy | light brown, cloudy | light brown, cloudy | light brown | light brown | OK |
| Log kill S. aureus diluted 1 + 49 with 10% manure max kill value 5 | 5/5 Trial1/Trial2 | 5/5 | 5/5 | 5/5 | 5/5 | 5/5 | 5/5 | 5/5 | 5/5 |
| Log kill E. coli diluted 1 + 49 with 10% manure max kill value 5 | 5/5 | 5/5 | 5/5 | 5/4 | 5/5 | 5/5 | 5/5 | 5/5 | 5/5 |
| pH | 3.14 | 3.09 | 3.17 | 2.81 | 2.81 | 2.50 | 3.21 | 3.28 | 3.34 |
| L/D Ratio | 502 | 624 | 803 | 651 | 625 | 929 | 3898 | 994 | 1105 |

TABLE 3

COMPOSITIONS CONTAINING LACTIC ACID AND AN ANIONIC SURFACTANT (% W/W)

|  | R | S | T | U | V |
|---|---|---|---|---|---|
| Lactic acid (adjusted to 100%) | 4.0 | 0 | 4.0 | 4.0 | 4.0 |
| Sodium Lauryl Sulfate (adjusted to 100%) | 4.0 | 0 | 2.0 | 0.0 | 0.0 |
| Sodium Octane Sulfonate (adjusted to 100%) | 0.0 | 2.2 | 2.0 | 0.0 | 4.0 |
| TOTAL (adjusted with water) | 100 | 100 | 100 | 100 | 100 |
| Log Kill S. aureus, 10% manure max kill value 5, 30 sec | 5 | 4 | 5 | 0 | 5 |
| Log Kill E. coli, 10% manure max kill value 5, 30 sec | 5 | 1 | 3 | 0 | 4 |

TABLE 4

COMPOSITIONS CONTAINING LACTIC ACID, FATTY ACID AND AN ANIONIC SURFACTANT (% W/W)

|  | W | X | Y | Z | AA | BB |
|---|---|---|---|---|---|---|
| Glutaraldehyde (adjusted to 100%) | 0 | 0 | 0 | 0.20 | 0.40 | 0.40 |
| Lactic acid (adjusted to 100%) | 1.60 | 4.00 | 0 | 4.00 | 4.00 | 4.00 |
| Sodium Octane Sulfonate (adjusted to 100%) | 0.00 | 4.00 | 0 | 2.00 | 0.00 | 4.00 |
| $C_9$-$C_{11}$ pareth-8 | 0.2 | 0 | 0.20 | 0 | 0 | 0 |
| Bronopol | 0.06 | 0 | 0.08 | 0 | 0 | 0 |
| Propionic acid | 0 | 0 | 1.60 | 0 | 0 | 0 |
| TOTAL (adjusted with water) | 100 | 100 | 100 | 100 | 100 | 100 |
| Log Kill S. aureus, 10% manure max kill value 5, 30 sec | 4.5/5 | 5 | 2/2 | 5 | 4 | 5 |
| Log Kill E. coli, 10% manure max kill value 5, 30 sec | 5/5 | 5 | 5 | 5 | 1 | 5 |

TABLE 5

COMPOSITIONS CONTAINING LACTIC ACID AND SODIUM LAURYL SULFATE

|  | CC | DD | EE | FF | GG | HH | II | JJ |
|---|---|---|---|---|---|---|---|---|
| Lactic acid (adj to 100%) | 0.35 | 0.5 | 0 | 1.5 | 0.25 | 0.1 | 2 | 0.17 |
| Sodium Lauryl Sulfate (adjusted to 100%) | 0.5 | 0.5 | 2 | 0 | 0.5 | 1 | 1 | 0.5 |
| TOTAL (adjusted with water) | 100 | 100 | 100 | 100 | 100 | 100 | 100 | 100 |
| Log Kill S. aureus no manure, AOAC, 30 sec |  |  | 0 |  |  |  |  |  |

TABLE 5-continued

COMPOSITIONS CONTAINING LACTIC ACID AND SODIUM LAURYL SULFATE

| | CC | DD | EE | FF | GG | HH | II | JJ |
|---|---|---|---|---|---|---|---|---|
| Log Kill E. coli no manure, AOAC, 30 sec | | | 0 | | | | | |
| Log Kill S. aureus 10% manure, AOAC, 5 min | >7.94 | | | | >7.94 | | | |
| Log Kill E. coli 10% manure, AOAC, 5 min | >7.97 | | | | >7.97 | | | |
| Log Kill S. aureus 10% manure, AOAC, 30 sec | | >7.94 | | 1.634 | | | | |
| Log Kill E coli 10% manure, AOAC, 30 sec | | 6.276 | | 0 | | | | |
| Log Kill S. aureus 20% manure, AOAC, 5 min | | >7.94 | | | | | >7.94 | |
| Log Kill E. coli 20% manure, AOAC, 5 min | | >7.97 | | | | | >7.97 | |
| Log Kill S. aureus 20% manure, AOAC, 30 sec | | 6.944 | | | | | | |
| Log Kill E. coli 20% manure, AOAC, 30 sec | | 6.674 | | | | | | |
| Log Kill S. aureus 10% manure, AOAC, 30 min | | | | | | >7.94 | | 7.246 |
| Log Kill E. coli 10% manure, AOAC, 30 min | | | | | | 0 | | |

Example 2

| CONCENTRATED COMPOSITIONS | | Lower Range (% w/w) | Upper Range (% w/w) |
|---|---|---|---|
| | Dilution Ratio | 1 + 19 V/V | 1 + 149 V/V |
| A germicide agent that retains activity in the presence of manure | $C_2$-$C_{14}$ carboxylic acids, such as propanoic acid (propionic acid), butanoic acid (butyric acid), pentanoic acid, hexanoic acid (caproic acid), heptanoic acid, octanoic acid (caprylic acid), nonanoic acid, decanoic acid (capric acid), endecanoic acid, dodecanoic acid (lauric acid), tridecanoic acid and tetradecanoic acid (myristic acid), lactic acid, citric acid, benzoic acid, malic acid, oxalic acid, tartaric acid, succinic acid, glutaric acid, valeric acid, glycolic acid and mixtures thereof. | 0.1 | 90 |
| Surfactant | Nonionic and anionic surfactants, such as alkane sulfonates, alkane sulfates, alkyl aryl sulfates, alkyl aryl sulfonates, sodium lauryl sulfate, sodium octane sulfonate, alcohol ethoxylates and mixtures thereof. | 0.1 | 40 |
| pH adjusting agents | Sulfuric acid, sulfurous acid, sulfamic acid, hydrochloric acid, phosphoric acid, phosphorous acid, $C_1$-$C_4$ fatty acids, citric acid, glycolic acid, lactic acid, acetic acid, benzoic acid, malic acid, oxalic acid, tartaric acid, succinic acid, glutaric acid, valeric acid, glycolic acid, sodium hydroxide, ammonium hydroxide, potassium hydroxide, sodium carbonate, sodium bicarbonate, monosodium acid diphosphonate and mixtures thereof. | 0 | 70 |
| Additional Germicide | Bronopol, chlorhexidine salts, triclosan, glycolic acid, lactic acid, polyhexamethyl biguanide, polyhexamethylene guanidine hydrochloride, polyhexamethylene guanidine hydrophosphate, poly[2-(2-ethoxy)-ethoxyethyl]-guanidinium | 0 | 25 |

-continued

CONCENTRATED COMPOSITIONS

| | | Lower Range (% w/w) | Upper Range (% w/w) |
|---|---|---|---|
| | chloride, benzyl alcohol, benzoic acid, N,N-bis(3-aminopropyl)alkylamines and mixtures thereof. | | |
| | Dye | 0 | 2 |
| Optional ingredients | Wetting agents, foaming agents, viscosity control agents, preservatives, skin conditioning agents, coupling agents, solvents and mixtures thereof. | 0 | 20 |

Example 3

READY TO USE COMPOSITIONS

| | | Lower Range (% w/w) | Upper Range (% w/w) |
|---|---|---|---|
| A germicide agent that retains activity in the presence of manure | $C_2$-$C_{14}$ carboxylic acids, such as propanoic acid (propionic acid), butanoic acid (butyric acid), pentanoic acid, hexanoic acid (caproic acid), heptanoic acid, octanoic acid (caprylic acid), nonanoic acid, decanoic acid (capric acid), endecanoic acid, dodecanoic acid (lauric acid), tridecanoic acid and tetradecanoic acid (myristic acid), lactic acid, citric acid, benzoic acid, malic acid, oxalic acid, tartaric acid, succinic acid, glutaric acid, valeric acid, glycolic acid and mixtures thereof. | 0.01 | 4 |
| Surfactant | Nonionic and anionic surfactants, such as alkane sulfonates, alkane sulfates, alkyl aryl sulfates, alkyl aryl sulfonates, sodium lauryl sulfate, sodium octane sulfonate, alcohol ethoxylates and mixtures thereof. | 0.01 | 4 |
| pH adjusting agents | Sulfuric acid, sulfurous acid, sulfamic acid, hydrochloric acid, phosphoric acid, phosphorous acid, $C_1$-$C_4$ fatty acids, citric acid, glycolic acid, lactic acid, acetic acid, benzoic acid, malic acid, oxalic acid, tartaric acid, succinic acid, glutaric acid, valeric acid, glycolic acid, sodium hydroxide, ammonium hydroxide, potassium hydroxide, sodium carbonate, sodium bicarbonate, monosodium acid diphosphonate and mixtures thereof. | 0 | 7 |
| Additional Germicide | Bronopol, chlorhexidine salts, triclosan, glycolic acid, lactic acid, polyhexamethyl biguanide, polyhexamethylene guanidine hydrochloride, polyhexamethylene guanidine hydrophosphate, poly[2-(2-ethoxy)-ethoxyethyl]-guanidinium chloride, benzyl alcohol, benzoic acid, N,N-bis(3-aminopropyl)alkylamines and mixtures thereof. | 0 | 2.5 |
| | Dye | 0 | 0.2 |
| Optional ingredients | Wetting agents, foaming agents, viscosity control agents, preservatives, skin conditioning agents, coupling agents, solvents and mixtures thereof. | 0 | 2 |

What is claimed is:

1. An aqueous composition for treatment or prevention of infectious hoof diseases, comprising:
   formic acid;
   from about 0.2% to about 1% by weight of lactic acid; and
   from about 0.2% to about 1% by weight of a nonionic or anionic surfactant selected from the group consisting of alkyl sulfates, alkyl aryl sulfates, alkyl aryl sulfonates, alkyl sulfonates, and alcohol ethoxylates,
   wherein the pH of said composition is less than about 5, wherein the composition retains germicidal activity in the presence of greater than 10% manure.

2. The composition of claim 1, further comprising one or more of a pH adjusting agent, a wetting agent, a foaming agent, a dye, a viscosity control agent, a preservative, a skin conditioning agent, a coupling agent and an additional solvent.

3. The composition of claim 1, further comprising a $C_2$-$C_{14}$ carboxylic acid selected from the group consisting of hexanoic acid, heptanoic acid, octanoic acid, nonanoic acid, decanoic acid, endecanoic acid, dodecanoic acid, tridecanoic acid, tetradecanoic acid, citric acid, benzoic acid, malic acid, oxalic acid, tartaric acid, succinic acid, glutaric acid, valeric acid and glycolic acid.

4. The composition of claim 1, further comprising an additional surfactant selected from the group consisting of alkyl sulfates, alkyl aryl sulfates, alkyl aryl sulfonates, alkyl sulfonates and alcohol ethoxylates.

5. The composition of claim 4, wherein the additional surfactant is selected from the group consisting of sodium lauryl sulfate, sodium octane sulfonate and $C_9$-$C_{11}$ pareth-8.

6. The composition of claim 1, further comprising a germicide selected from the group consisting of N,N-bis(3-aminopropyl) $C_6$-$C_{18}$ alkyl amines, bronopol, chlorhexidine salts, triclosan, glycolic acid, polyhexamethyl biguanide, polyhexamethylene guanidine hydrochloride, polyhexamethylene guanidine hydrophosphate, poly[2-(2-ethoxy)-ethoxyethyl]-guanidinium chloride, benzyl alcohol, benzoic acid and mixtures thereof.

7. A method for treating or preventing infectious hoof diseases, comprising:
   topically administering a therapeutically effective amount of an aqueous composition comprising:
   formic acid,
   from about 0.2% to about 1% by weight of lactic acid,
   from about 0.2% to about 1% by weight of a nonionic or anionic surfactant selected from the group consisting of: alkyl sulfates, alkyl aryl sulfates, alkyl aryl sulfonates, alkyl sulfonates, and alcohol ethoxylates,
   wherein the pH of said composition is less than about 5, to one or more hooves of an animal,
   wherein the step of administering occurs with the hoof or hooves in a natural state.

8. The method of claim 7, wherein the composition further comprises a $C_2$-$C_{14}$ carboxylic acid selected from the group consisting of hexanoic acid, heptanoic acid, octanoic acid, nonanoic acid, decanoic acid, endecanoic acid, dodecanoic acid, tridecanoic acid, tetradecanoic acid, citric acid, benzoic acid, malic acid, oxalic acid, tartaric acid, succinic acid, glutaric acid, valeric acid and glycolic acid.

9. The method of claim 7, wherein the composition further comprises an additional surfactant selected from the group consisting of alkyl sulfates, alkyl aryl sulfates, alkyl aryl sulfonates, alkyl sulfonates and alcohol ethoxylates.

10. The method of claim 7, wherein the hoof disease is selected from papillomatous digital dermatitis, interdigital phlegmon, interdigital dermatitis, laminitis, white line disease and heel erosion.

11. The method of claim 7, wherein the aqueous composition further comprises a germicide selected from the group consisting of N,N-bis(3-aminopropyl) $C_6$-$C_{18}$ alkyl amines, bronopol, chlorhexidine salts, triclosan, glycolic acid, polyhexamethyl biguanide, polyhexamethylene guanidine hydrochloride, polyhexamethylene guanidine hydrophosphate, poly[2-(2-ethoxy)-ethoxyethyl]-guanidinium chloride, benzyl alcohol, benzoic acid and mixtures thereof.

12. The method of claim 7, wherein the composition is administered as one of a spray, a foam, a gel, an ointment, a cream, a footbath or a footwrap.

13. The composition according to claim 1, wherein said alkyl sulfonate is a sodium $C_{14}$-$C_{16}$ α-olefin sulfonate.

14. The method according to claim 7, wherein said alkyl sulfonate is a sodium $C_{14}$-$C_{16}$ α-olefin sulfonate.

* * * * *